US008133228B2

(12) United States Patent
Bharadwaj et al.

(10) Patent No.: US 8,133,228 B2
(45) Date of Patent: Mar. 13, 2012

(54) CHISEL SYSTEM FOR OSTEOCHONDRAL IMPLANTS AND A SURGICAL PROCEDURE INVOLVING SAME

(75) Inventors: Jeetendra Subhash Bharadwaj, Memphis, TN (US); Jeffrey H. Nycz, Warsaw, IN (US); Daniel Andrew Shimko, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 493 days.

(21) Appl. No.: 12/352,260

(22) Filed: Jan. 12, 2009

(65) Prior Publication Data
US 2009/0118750 A1 May 7, 2009

Related U.S. Application Data

(62) Division of application No. 11/343,156, filed on Jan. 30, 2006, now Pat. No. 7,497,861.

(51) Int. Cl.
*A61B 17/00* (2006.01)

(52) U.S. Cl. ............. 606/79; 606/83; 606/84; 606/86 R

(58) Field of Classification Search ............... 606/79, 606/83, 84, 86 R
See application file for complete search history.

(56) References Cited

U.S. PATENT DOCUMENTS

| 5,059,195 | A | 10/1991 | Gray |
| 5,957,946 | A | 9/1999 | Shuler et al. |
| 5,961,522 | A | 10/1999 | Mehdizadeh |
| 6,017,348 | A * | 1/2000 | Hart et al. ............ 606/79 |
| 6,306,142 | B1 | 10/2001 | Johanson et al. |
| 2006/0009774 | A1 | 1/2006 | Goble et al. |
| 2007/0149982 | A1 | 6/2007 | Lyons |
| 2007/0172506 | A1 | 7/2007 | Nycz et al. |
| 2007/0173846 | A1 | 7/2007 | Bharadwaj et al. |
| 2007/0173852 | A1 | 7/2007 | Gil |
| 2007/0173880 | A1 | 7/2007 | Nycz et al. |
| 2007/0191852 | A1 | 8/2007 | Shimko et al. |

* cited by examiner

*Primary Examiner* — Eduardo C Robert
*Assistant Examiner* — Ellen C Hammond

(57) ABSTRACT

A chisel system for harvesting an implantable graft from an area of a human having a cartilage overlying a condyle, according to which a module is provided that has one end connected to a handle. A cutting surface is formed at the other end of the module that cuts through the cartilage and condyle.

4 Claims, 2 Drawing Sheets

CHISEL SYSTEM FOR OSTEOCHONDRAL IMPLANTS AND A SURGICAL PROCEDURE INVOLVING SAME

This application is a divisional of co-pending U.S. application Ser. No. 11/343,156, Jan. 30, 2006, the entire contents of which are hereby incorporated by reference.

BACKGROUND

This invention relates to a chisel system and, more particularly, to an improved modular chisel system for cutting an opening to receive an implant in an osteochondral implant procedure.

In the human body, the knee consists of three articulating components—a femur, a tibia, and a patella—that are held in place by various ligaments. The corresponding chondral areas of the femur and the tibia form a hinge joint, and the patella protects the joint. Portions of the latter areas, as well as the underside of the patella, are covered with an articular cartilage, which allow the femur and the tibia to smoothly glide against each other without causing damage.

The articular cartilage often tears, usually due to traumatic injury (often seen in athletics) and degenerative processes (seen in older patients). This tearing does not heal well due to the lack of nerves, blood vessels and lymphatic systems; and the resultant knee pain, swelling, and limited motion of the bone(s) must be addressed.

Damaged adult cartilages have historically been treated by a variety of surgical interventions including lavage, arthroscopic debridement, and repair stimulation, all of which provide less than optimum results.

Another known treatment involves removal and replacement of the damaged cartilage with a prosthetic device. However, the known artificial prostheses have largely been unsuccessful since they are deficient in the elastic, and therefore in the shock-absorbing, properties characteristic of the cartilage. Moreover, the known artificial devices have not proven able to withstand the forces inherent to routine knee joint function.

In an attempt to overcome the problems associated with the above techniques, osteochondral transplantation, also known as "mosaicplasty" or "OATS" has been used to repair articular cartilages. This procedure involves removing injured tissue from the articular defect and drilling cylindrical openings in the base of the defect and underlying bone. Cylindrical plugs or grafts, consisting of healthy cartilage overlying bone, are usually obtained by using a chisel to punch them out from another area of the patient, typically from a lower load-bearing region of the joint under repair, or from a donor patient. The harvested grafts are then implanted in the openings.

In these cases, the chisels used to harvest the grafts are, for the most part, one-piece designs that consist essentially of a blade portion extending from a handle portion. Thus, once the grafts are harvested, they remain in the hollow, distal end portion of the chisel and must be removed from that end. This often causes damage to the graft, and in most cases to the cartilage portion of the graft.

Also, the cutting end of the chisels are blunt and thus can cause damage, in the form of high mechanical deformation, as the cartilage portion of the graft is punched out during the harvesting procedure. Further, each chisel can cut only one size graft, which requires a series of chisels for cutting a series of grafts having different dimensions. However, to provide a separate chisel for each size graft is expensive.

Therefore what is needed is a chisel system that overcomes the above problems.

DETAILED DESCRIPTION

Figure 1:
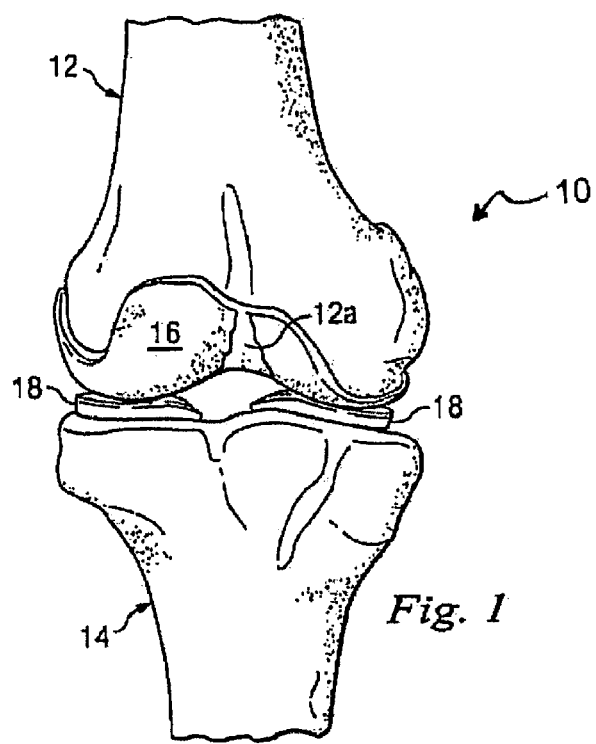
FIG. 1 is an elevational view of a human knee with certain parts removed in the interest of clarity.

Referring to FIG. 1 of the drawing, the reference numeral 10 refers, in general, to a knee area of a human including a femur 12 and a tibia 14 whose respective chondral areas are in close proximity. A cartilage 16 extends over a portion of the chondral area of the femur 12, and a meniscus 18 extends between the cartilage and the tibia. The patella, as well as the tendons, ligaments, and quadriceps that also form part of the knee are not shown in the interest of clarity.

It will be assumed that a portion of the cartilage 16 extending over a chondral area 12a of the femur 12 has been damaged and removed by the surgeon, or has worn away, and it is desired to harvest a graft from another area of the patient/recipient, such as an undamaged non-load bearing area of the femur or tibia, or from a corresponding area of a donor. It will also be assumed that an opening is formed in the defect 12a for receiving the graft.

Figure 2:
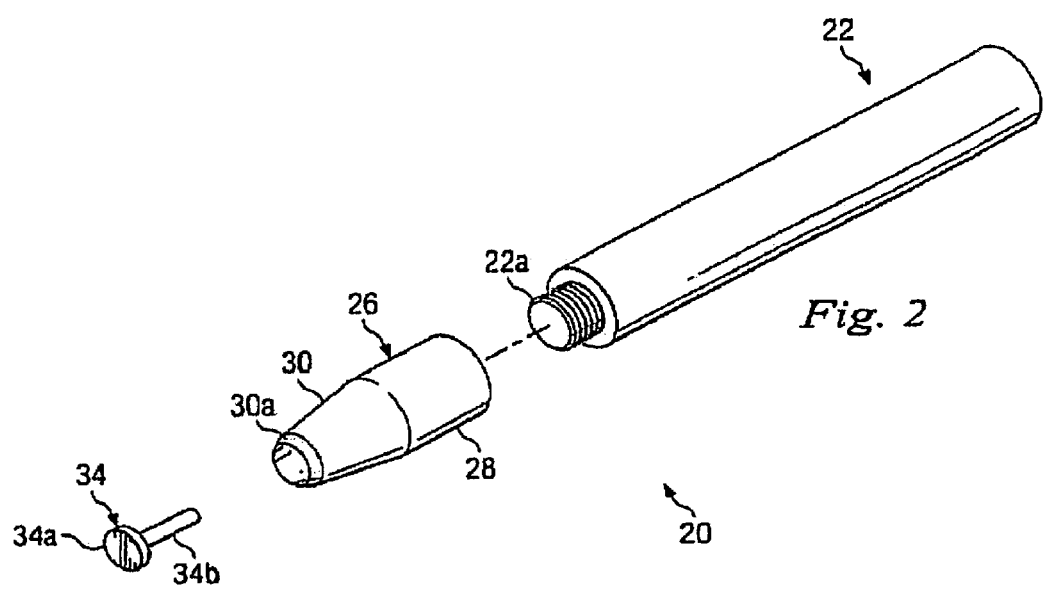
FIG. 2 is an isometric, exploded view of a modular chisel system according to an embodiment of the invention.

Referring to FIG. 2, a chisel system for harvesting the graft is referred to, in general, by the reference numeral 20 and includes a cylindrical handle 22 having an externally-threaded, reduced-diameter nipple 22a extending from one end thereof.

Figure 3:
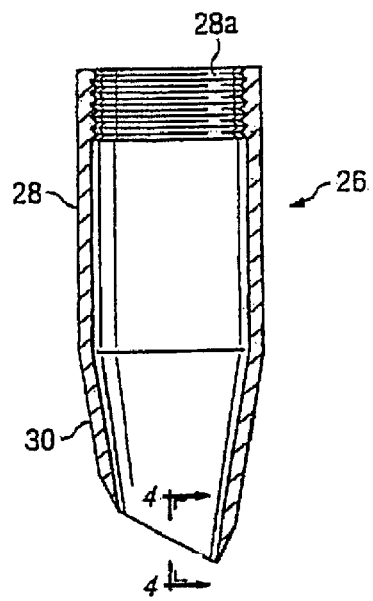
FIG. 3 is an enlarged cross-sectional view of the cutting module of the system of FIG. 2.

As shown in FIGS. 2 and 3, a cutting module 26 is provided that consists of a hollow cylindrical member 28, the inner surface of one end portion of which is internally threaded as shown by the reference numeral 28a, and is sized to receive the nipple 22a in threaded engagement. A hollow, frusto-conical member 30 extends from the other end of the member 28 and is formed integrally with the latter member.

A tap member 34 (FIG. 2) is also provided and consists of an enlarged head 34a disposed at one end of a solid rod, or shank, 34b. The diameter of the shank 34b is slightly less than the inner diameter of the distal end of the member 30, for reasons to be described. The tap member 34 is not connected to the module 26, but rather is used to remove a harvested graft from the module in a manner to be described.

Figure 4:
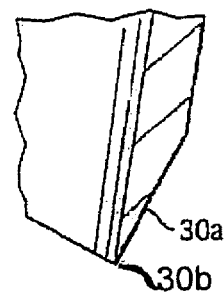
FIG. 4 is a cross-sectional view taken along the line 4-4 of FIG. 3.

As shown in FIGS. 3 and 4, the distal end portion of the member 30 is cut at an angle to form an end 30a that extends at an angle to the axis of the member. Also, the cross section of the angled end portion is tapered radially inwardly to form a relatively sharp cutting surface, or edge, 30b, for reasons to be described.

To initiate the harvesting procedure, the handle 22 (FIG. 2) is grasped and the chisel system 20 is brought down to a non-damaged area of the patient/recipient, or of a donor, such as an undamaged non-load bearing area of the femur or tibia, having a cartilage overlying a condyle. The chisel system 20 is placed perpendicularly to the latter area and forced down into the cartilage. The sharpness of the cutting edge 30b is such that it slices through the layer of cartilage. The manual force is continued and could be increased as necessary so that the cutting edge also cuts through the condyle until the desired depth is attained. During this time, the severed cartilage and condyle next to the cartilage enter the hollow distal end portion of the member 30 and move axially in the latter member. When the desired depth of cut is attained, the handle 22 is manipulated as necessary to completely sever the corresponding end of the condyle thus forming a plug, or graft (not shown) extending in the interior of the module 26.

The module 26 is then removed from the handle 22 by unscrewing the module, and the distal end of the shank 34b of the tap 34 is then pushed into the distal end of the member 30 where it engages the end of the condyle portion of the graft. Further pushing advances the graft though the member 30 and then though the member 28 in a direction towards the threaded end portion of the latter member. The graft is then removed from the module 30 and is ready to be treated for implantation in an opening to be formed in the defect 12a (FIG. 1).

It is understood that, during the above harvesting procedure, any of the meniscus 18 (FIG. 1) or related tendons, ligaments and quadriceps are removed or pushed aside as necessary to permit access to the above area to permit the harvesting of the graft.

Other modules can be provided that are identical to the module 26, but have a member similar to member 30, but with a cutting edge of a cross-section that is different than the diameter of the cutting edge 30a. Thus, the chisel system 20 can be provided as a kit, having one handle 22 and several modules 26, each having a different diameter cutting surface, depending on the size of the graft to be harvested.

Figure 5:
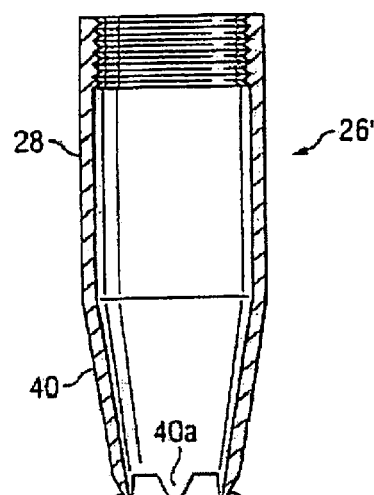
FIGS. 5 and 6 are views, similar to that of FIG. 3, but depicting alternate embodiments of the cutting module of FIG. 3.

An alternate embodiment of the module 26 is referred to in FIG. 5 by the reference numeral 26', and includes a member 28 that is identical to the member 28 of the embodiment of FIGS. 2-4. According to the embodiment of FIG. 5, a hollow, frusto-conical member 40 is provided that extends from the other end of the member 28 and is formed integrally with the latter member. A series of angularly-spaced cutting teeth 40a are formed at the distal end of the member 40 to form a saw tooth design. Each tooth 40a is tapered inwardly towards its end to define relatively sharp points and cutting edges for cutting the graft.

The harvesting procedure is initiated by bringing the module 26' into engagement with the cartilage portion of the graft to be harvested, and applying manual force so that the teeth 44a cut into the layer of cartilage portion and then through the condyle portion of the graft. The harvesting is then completed in accordance with the procedure discussed above and the tap 34 (FIG. 2) can be used to remove the harvested graft from the member 40, also in the same manner as described above.

Figure 6:
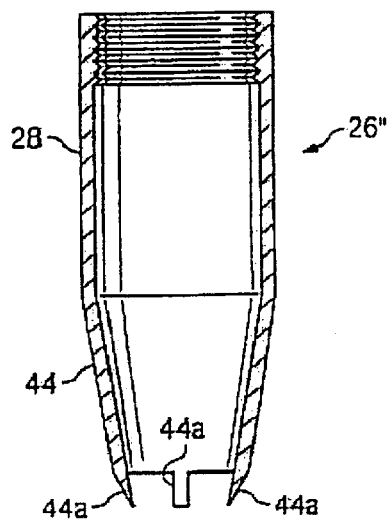

Another alternate embodiment of the module 26 is referred to in FIG. 6 by the reference numeral 26", and includes a member 28 that is identical to the member 28 of the embodiment of FIGS. 2-4. According to the embodiment of FIG. 5, a hollow, frusto-conical member 44 is provided that extends from the other end of the member 28 and is formed integrally with the latter member. Three angularly-spaced prongs 44a are formed at the distal end of the member 40 and are dimensioned to form sharp points and cutting edges.

The harvesting procedure is initiated by bringing the module 26" into engagement with the cartilage portion of the graft to be harvested and applying manual force so that the prongs 44a cut into the cartilage portion. Then, the handle 22 (FIG. 2) is rotated, causing the edges of the prongs to cut through any remaining portion of the cartilage and through the condyle portion of the graft to be harvested. The harvesting is then completed in accordance with the procedure discussed above, and the tap 34 (FIG. 2) can be used to remove the harvested graft from the member 40, also in the same manner as described above.

It can be appreciated that the above-mentioned kit can also include the modules 26' and 26", as well as variations thereof, so that the cutting surfaces can be varied in accordance with the particular application.

VARIATIONS

1. The size and shape of the cutting surfaces at the end of the members 30, 40 and 44 can vary. For example. the surfaces can have elliptical shape, a rectangular shape, or the like.

2. The configurations of the cutting surfaces at the end of the members 30, 40 and 44 can vary.

3. The number of teeth 40a and prongs 44a of the embodiments of FIGS. 5 and 6, respectively, can vary, as well as their size and/or shape.

4. The spatial references mentioned above, such as "upper", "lower", "under", "over", "between", "outer", "inner" and "surrounding" are for the purpose of illustration only and do not limit the specific orientation or location of the components described above.

5. The present invention is not limited to use with knees of humans but rather is applicable other damaged areas of all animals.

6. The graft discussed above can be harvested or prepared from another area of the patient/recipient, from another human, or from any number of anatomic sites, animal or otherwise.

7. The method and device disclosed above can be used in any surgical or experimental situation (animal species or otherwise) to harvest grafts in any anatomic region containing cartilage or bone.

Those skilled in the art will readily appreciate that many other variations and modifications of the embodiment described above can be made without materially departing from the novel teachings and advantages of this invention. Accordingly, all such variations and modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A surgical procedure for harvesting an implantable graft from an area of a human having a cartilage overlying a condyle, the procedure comprising:
    obtaining a generally cylindrical cutting module having a proximal portion, central portion, and a distal portion, wherein the proximal portion comprises a cutting surface, at least part of the interior of the distal portion being threaded, the central portion having an outer surface with an outer diameter and an inner surface defining an inner bore with a first inner diameter, the proximal portion having an inner surface and an outer surface, the inner surface of the proximal portion tapering inwardly with respect to the inner bore of the central portion to a second inner diameter less than the first inner diameter;
    threadingly connecting the distal portion of the cutting module to a threaded portion of a handle to form a chisel;
    grasping the handle and engaging the cutting surface with a bone material also containing cartilage;
    applying force to cut through the cartilage and condyle to form a graft;

removing the cutting module from the handle;
inserting a tap into the proximal portion of the cutting module; and
pushing the graft out of the cutting module through the distal portion, thereby removing the graft without contacting the cartilage portion of the graft.

2. The surgical procedure according to claim 1, further comprising rotating the cutting surface to cut through cartilage or bone of the graft.

3. The surgical procedure according to claim 1, further comprising threadingly disconnecting the cutting module from the handle prior to inserting the tap.

4. The surgical procedure according to claim 1, further comprising applying a manual force to the handle.

* * * * *